US009028122B2

(12) United States Patent
Tuchrelo et al.

(10) Patent No.: US 9,028,122 B2
(45) Date of Patent: May 12, 2015

(54) LIGHTED ELECTRICAL CONNECTOR ASSEMBLY

(75) Inventors: Robert Tuchrelo, Williamson, NY (US); Jeffrey Cahoon, Williamson, NY (US)

(73) Assignee: Idea Boxx, LLC, Victor, NY (US)

(*) Notice: Subject to any disclaimer, the term of this patent is extended or adjusted under 35 U.S.C. 154(b) by 46 days.

(21) Appl. No.: 13/476,559

(22) Filed: May 21, 2012

(65) Prior Publication Data

US 2013/0308304 A1 Nov. 21, 2013

(51) Int. Cl.

| | |
|---|---|
| ***F21V 33/00*** | (2006.01) |
| ***A61B 1/24*** | (2006.01) |
| ***F21K 2/00*** | (2006.01) |
| ***F21V 5/00*** | (2006.01) |
| ***G01C 9/32*** | (2006.01) |
| ***F21V 17/06*** | (2006.01) |
| *H01R 13/66* | (2006.01) |
| *H01R 13/70* | (2006.01) |
| *H01R 13/717* | (2006.01) |

(52) U.S. Cl.

CPC ........ *H01R 13/7175* (2013.01); *H01R 13/6675* (2013.01); *H01R 13/70* (2013.01); *H01R 13/7172* (2013.01); *H01R 2201/06* (2013.01)

(58) Field of Classification Search

CPC ........................ H01R 13/7175; H01R 13/7172

USPC ................................. 362/577, 437, 439, 253

See application file for complete search history.

(56) References Cited

U.S. PATENT DOCUMENTS

| | | | | |
|---|---|---|---|---|
| 5,242,315 | A | 9/1993 | O'Dea | |
| 5,340,338 | A | 8/1994 | Sai et al. | |
| 5,470,252 | A | 11/1995 | Fladung | |
| 6,089,893 | A | 7/2000 | Yu et al. | |
| 6,095,970 | A | 8/2000 | Hidaka et al. | |
| 6,319,051 | B1 | 11/2001 | Chang et al. | |
| 6,336,825 | B1 * | 1/2002 | Seefried | 439/488 |
| 6,457,992 | B2 | 10/2002 | Posey et al. | |
| 6,474,999 | B1 | 11/2002 | Givens et al. | |
| 6,690,804 | B2 | 2/2004 | Everett | |

(Continued)

FOREIGN PATENT DOCUMENTS

| | | |
|---|---|---|
| JP | 10-247560 | 9/1998 |
| JP | 20011519077 A | 10/2001 |

OTHER PUBLICATIONS

International Search Report in corresponding PCT Application No. PCT/US2012/048692 dated Mar. 12, 2013 (4 pages).

(Continued)

*Primary Examiner* — Peggy Neils
*Assistant Examiner* — William N Harris
(74) *Attorney, Agent, or Firm* — Brian B. Shaw, Esq.; Timothy W. Menasco, Esq.; Harter Secrest & Emery LLP

(57) ABSTRACT

An electrical connector assembly, comprising an electrical conductor a housing enclosing a portion of the conductor, the housing having a terminal end; a connector connected to the conductor and the housing, the connector extending along a longitudinal axis from the terminal end of the housing, the connector having a terminal surface spaced from the housing, a light emitter within the housing, and a light guide within the housing to direct light from the light emitter to exit the housing from the terminal end to substantially illuminate the connector along the longitudinal axis.

16 Claims, 5 Drawing Sheets

(56) References Cited

U.S. PATENT DOCUMENTS

| | | | | |
|---|---|---|---|---|
| 6,699,065 | B1 | 3/2004 | Espenshade et al. | |
| 6,733,333 | B1 | 5/2004 | Chen | |
| 6,752,649 | B2 | 6/2004 | Arkin et al. | |
| 6,921,284 | B2 | 7/2005 | Sirichai et al. | |
| 7,004,595 | B1 | 2/2006 | Stoddard | |
| 7,036,948 | B1 | 5/2006 | Wyatt | |
| 7,175,327 | B1 | 2/2007 | Tsai | |
| 7,628,619 | B2 | 12/2009 | Chuang | |
| 7,744,231 | B2 * | 6/2010 | Hutchinson et al. | 362/95 |
| 7,976,336 | B2 | 7/2011 | Yang et al. | |
| 8,128,558 | B2 | 3/2012 | Amling et al. | |
| 8,303,333 | B2 | 11/2012 | Lee | |
| 8,475,203 | B2 | 7/2013 | Wu | |
| 8,823,540 | B2 | 9/2014 | Scholeno | |
| 2004/0042735 | A1 | 3/2004 | Ma | |
| 2007/0268688 | A1 | 11/2007 | Chen | |
| 2008/0249363 | A1 | 10/2008 | Nakamura et al. | |
| 2008/0316697 | A1 * | 12/2008 | Zhu | 361/684 |
| 2009/0042433 | A1 | 2/2009 | Bushby | |
| 2010/0021639 | A1 | 1/2010 | Kamperman et al. | |
| 2010/0265712 | A1 * | 10/2010 | Singh et al. | 362/253 |
| 2010/0309657 | A1 * | 12/2010 | Purdy et al. | 362/200 |
| 2011/0256769 | A1 | 10/2011 | Wu | |
| 2012/0202385 | A1 | 8/2012 | Miyagi et al. | |
| 2012/0289080 | A1 | 11/2012 | Huang et al. | |
| 2013/0171875 | A1 | 7/2013 | Kwon | |

OTHER PUBLICATIONS

Written Opining of the International Searching Authority in corresponding PCT Application No. PCT/US2012/048692 dated Mar. 12, 2013 (5 pages).

Brand New CP Technologies CP-USB2-AB—Ebay website (2 pages) http://www.ebay.com/itm/Brand-NEW-CP-Technologies-CP-USB2-AB-6L-Illuminated-USB-2-0. . .

EL Illuminated USB Charging Cable for Apple iPhone iPad Like Dexim Sockitz—Ebay website (5 pages) http://www.ebay.com/...d-USBCharging-Cable-for-Apple-iPhone-iPod. . .

Wikipedia—Universal Serial Bus (33 pages) http://en.wikipedia.org/wiki/Usb.

Wikipedia—Technology (5 pages) http://en.wikipedia.org/wiki/USB_flash_drive.

Office Action in corresponding U.S. Appl. No. 13/823,579 dated Nov. 5, 2014 (14 pages).

* cited by examiner

LIGHTED ELECTRICAL CONNECTOR ASSEMBLY

CROSS-REFERENCE TO RELATED APPLICATIONS

None.

STATEMENT REGARDING FEDERALLY SPONSORED RESEARCH OR DEVELOPMENT

None.

REFERENCE TO A "SEQUENCE LISTING"

None.

BACKGROUND OF THE INVENTION

1. Technical Field

The present system relates to electrical connector assemblies and more specifically to lighted connector assemblies having a connector and a light guide that illuminates a connector and a separate receptacle to aid in locating the connector in the receptacle.

2. Description of the Related Art

Electrical connector assemblies are used for a multitude of purposes. Universal Serial Bus (USB) electrical connector assemblies, for example, permit communication between a computer and electrical devices. USB is an external computer interface industrial standard that defines the communication protocols, cables and connectors that enables such communication between devices. Typically, a USB receptacle, which is a male receiving portion, mounts to a computer or other device for receiving a USB connector or plug of an electrical connector assembly. USB devices, for example, may be connected to a USB receptacle of a computer using a USB cable having two terminal ends with USB plugs inserted into the USB receptacles of the computer and electrical device.

Most computers today include multiple USB receptacles for connecting USB devices such as PDAs, cellular phones and video game consoles, and for connecting computer peripherals to permit communication between the computer and printers, scanners, keyboards, pointing devices, and external hard drives. USB receptacles also permit communication between computers and mass storage devices, often referred to as a flash drive or a thumb drive, for storing large quantities of data. Even certain LED, Plasma and LCD televisions now include multiple USB receptacles.

USB cabling has eliminated the need for a separate power charger for a portable device since power is provided from the computer to the device by the USB cable. Some cable connectors include lights, which indicate when power is received from the computer. Thus, one knows when the USB cable is successfully connected to the computer. However, since power is not provided until after the USB cable is plugged into the receptacle, this light cannot be used to illuminate the USB receptacle when inserting the connector into the receptacle. Since USB receptacles are small and often in discrete locations that are not well-lit, many find it difficult to align and insert connectors into receptacles. Further, because it is difficult to see the receptacle receiving the connector, it is easy to insert the connector into a wrong-sized receptacle or misalign the connector and receptacle, thereby bending the connector or damaging the pins inside the connector and receptacle.

What is needed, then, is an electrical connector assembly that emits light to substantially illuminate the connector and corresponding receptacles to facilitate the interconnection of the connector and receptacle. Also needed is a lighted electrical connector assembly that is configured to attach to a preexisting USB connector. The need also exists for a battery powered electrical connector assembly capable of emitting light from a terminal end of the housing to substantially illuminate the connector and corresponding receptacle when power from the computer is not yet available.

BRIEF SUMMARY OF THE INVENTION

The electrical connector assembly of the present system provides for illumination of a plug and receptacle during insertion.

In one configuration, the electrical connector assembly includes an electrical conductor, a housing, a connector, a light emitter, and a light guide. The housing encloses a portion of the conductor and includes a terminal end. The connector is connected to the conductor and the housing and extends along a longitudinal axis from the terminal end of the housing. The connector further includes a terminal surface spaced from the housing. The light emitter and a portion of the light guide are disposed within the housing. The light guide directs light from the light emitter to exit the housing from the terminal end to substantially illuminate the connector along the longitudinal axis.

In one configuration, the light guide directs a portion of the light to intersect a portion of the connector. The electrical connector assembly in another configuration includes the light guide directing a portion of the light to pass from the terminal end within a periphery of the connector.

The electrical connector assembly can supply power to the light emitter. For example, in one configuration, the electrical conductor includes a battery in the housing for supplying power to the light emitter.

DETAILED DESCRIPTION OF THE INVENTION

Figure 1:
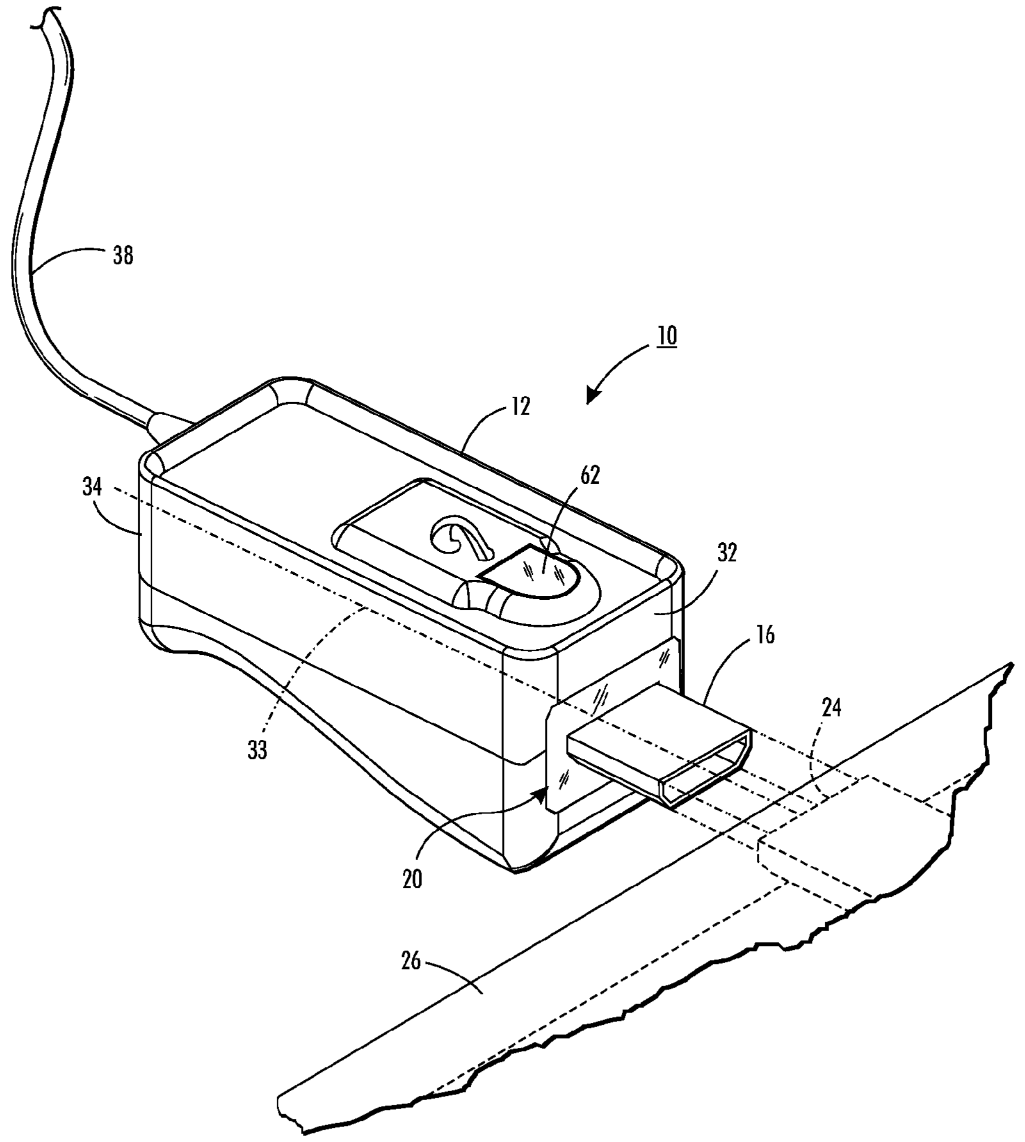
FIG. 1 is a perspective view of a configuration of an electrical connector assembly.

At the outset, it should be appreciated that the use of the same reference number throughout the several figures designates a like or similar element.

Referring now to the Figures, an electrical connector assembly 10 includes a housing 12, an electrical conductor 14, a connector 16, a light emitter 18, and a light guide 20 or 82. The light guide 20 or 82 directs light from the light emitter 18 towards a terminal surface 22 of the connector 16 to illuminate a receptacle 24 mounted on a device 26 receiving the connector 16, for example a computer.

Figure 3:
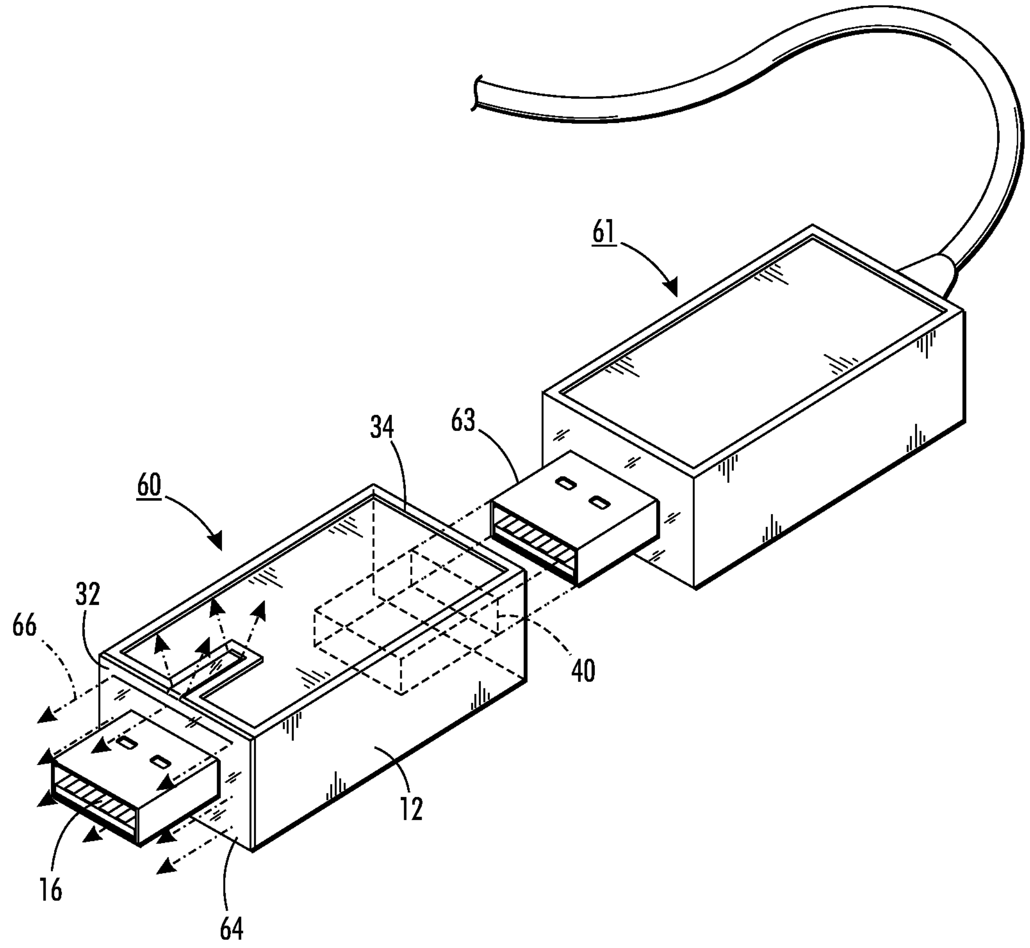
FIG. 3 is a perspective view of the electrical connector assembly illustrating the electrical connector assembly aligned for attaching to a USB cable.
Figure 4:
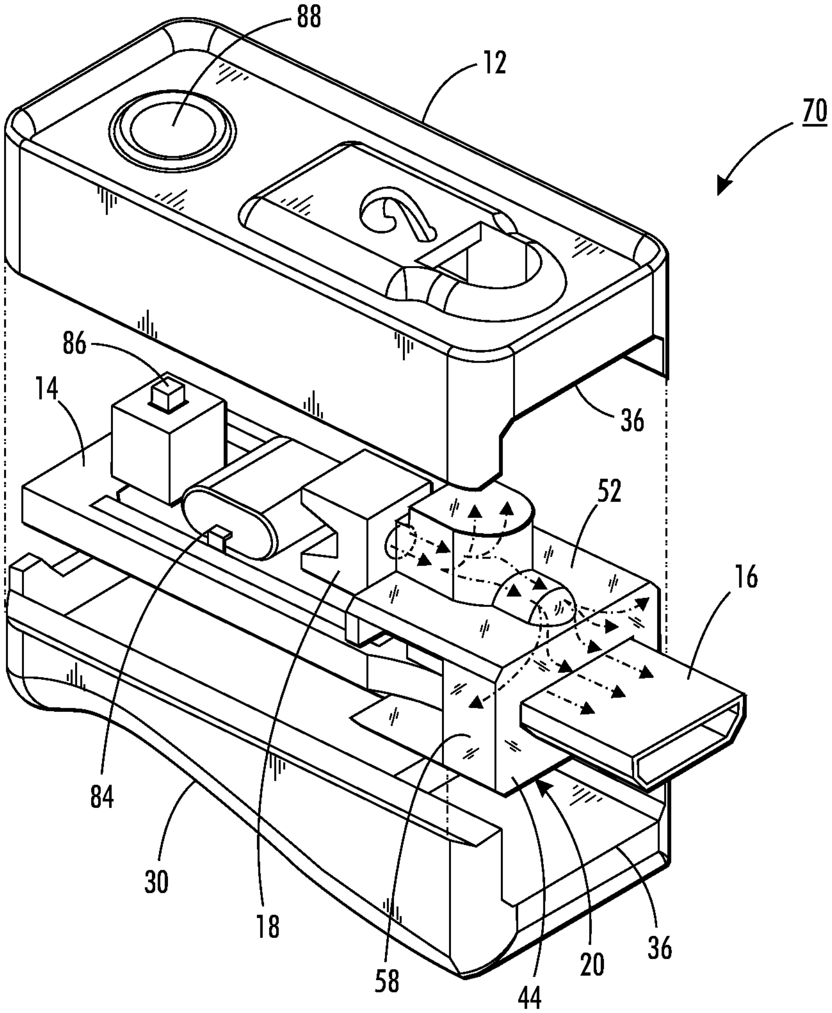
FIG. 4 is an exploded schematic view of another configuration of the electrical connector assembly illustrating a battery operated electrical connector assembly.
Figure 5:
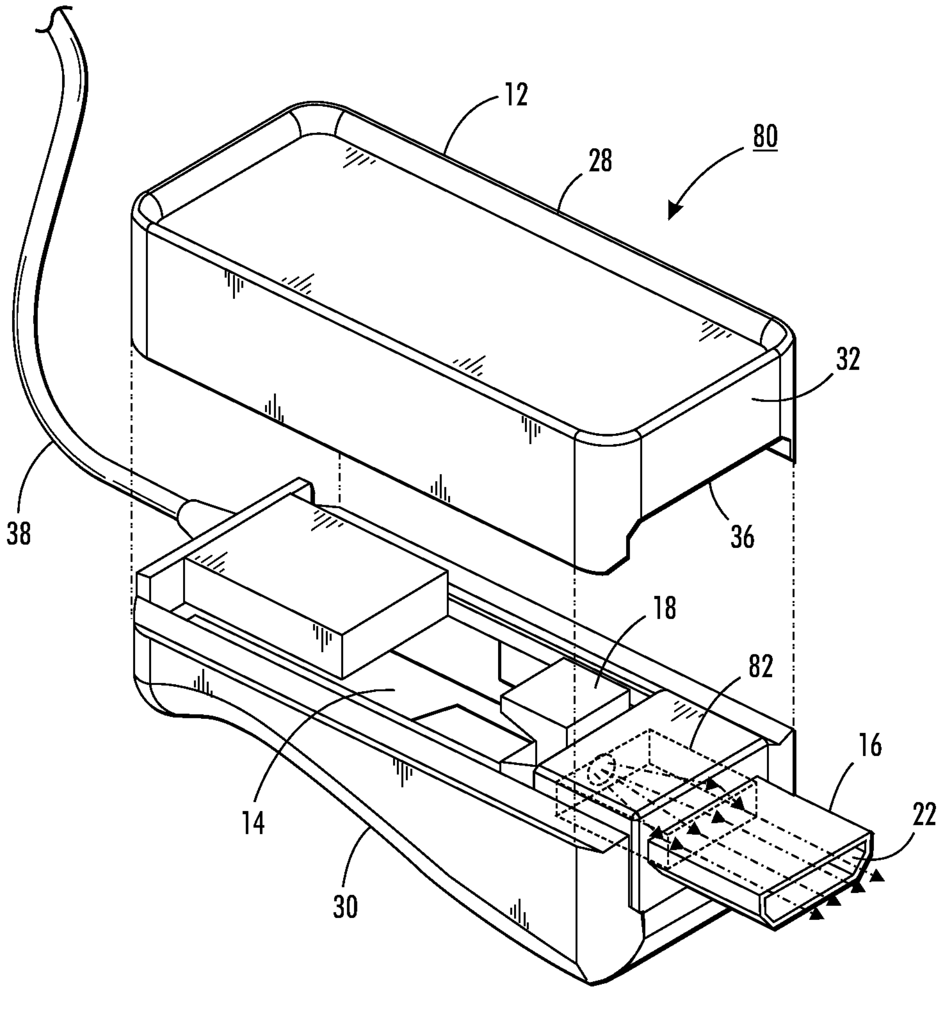
FIG. 5 is an exploded schematic view of yet another configuration of the electrical connector assembly illustrating a light guide directing light within a periphery of a connector.

Without limiting the scope of the disclosure, the electrical connector assembly 10 is set forth in terms of a USB electrical connector assembly having a standard USB connector 16 connected to the electrical conductor 14, and includes, but is not limited to USB cables, charging cables, mass storage devices and lighted attachments. For example, as shown in FIGS. 1 and 5, the electrical connector assemblies 10 and 80, respectively, are each a USB cable having at least one end with a USB plug. Either one end or multiple ends of the cable may include the light emitter 18 and light guide 20, 82 for illuminating receptacle region(s) of a computer 26 and/or other host device. In another configuration, as shown in FIG. 4, the electrical connector assembly 10 is a mass storage device, such as a flash drive. Alternatively, the electrical connector assemblies 50, 60 are stand alone attachments for a USB cable 61 having a USB plug 63. The electrical connector assemblies 50, 60 each serve as an intermediate component between the USB plug 63 and the computer 26 or other host device. The electrical connector assemblies 50, 60 illuminate the connector 16 and the receptacle 24, as shown in the configurations illustrated in FIGS. 2 and 3, respectively. The USB cable 61 may include a "twisted pair" of wires having "Data+" and "Data−" conductors twisted together in a double helix, as well known in the art.

Figure 2:
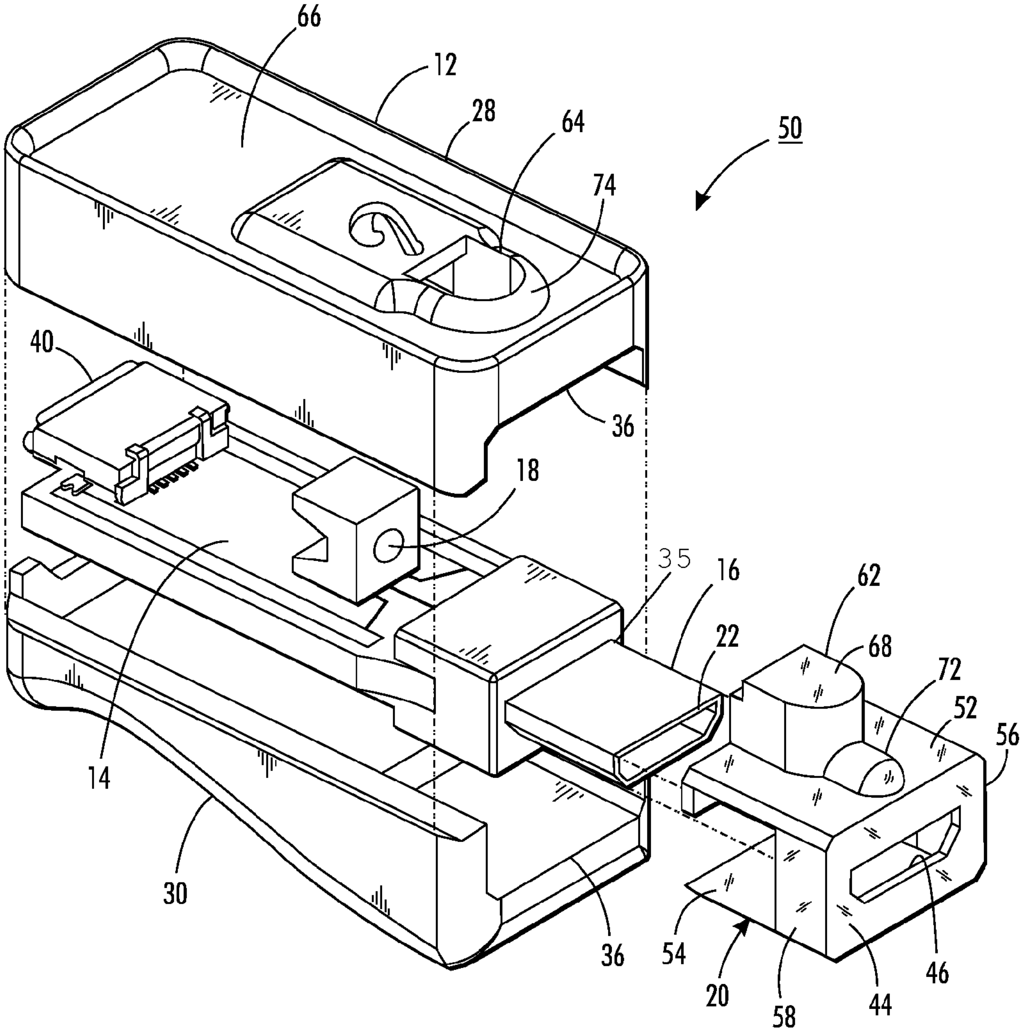
FIG. 2 is an exploded schematic view of the electrical connector assembly shown in FIG. 1, except illustrating a connector box rather than a cable.

As shown in the Figures, the housing 12 is dimensioned for enclosing the electrical conductor 14 and the light emitter 18. The housing 12 may include an upper housing 28 and the lower housing 30 as shown in FIGS. 1, 2, 4 and 5. Alternatively, the upper housing 28 and lower housing 30 may be integral as shown in FIG. 3. In both configurations, the housing 12 includes a terminal end 32, a longitudinal axis 33 and a front end 34. The connector 16 extends along the longitudinal axis 33 of the terminal end 32, wherein a front end 35 of the connector 16 aligns with and is adjacent to the terminal end 32 of the housing 12. In certain embodiments, the upper housing 28 and lower housing 30 include notches 36 through which the connector 16 extends. Without limiting the scope of the disclosure, the front end 34, may include a cable 38 as shown in FIG. 1 or a connector box 40, as shown in FIGS. 2 and 3 for connecting the electrical connector assembly 50 or 60 to another cable. The connector box 40, in one configuration, is a USB receptacle configured for receiving a USB connector.

The housing 12 is preferably substantially opaque such that light does not pass through the housing. The light guide directs light towards the terminal end 32 of the housing and additionally or alternatively, within a periphery of the connector 16 from the terminal end 32 of the electrical connector assembly 80 through the terminal surface 22 of the connector 16 as described in more detail below.

As illustrated in the Figures, the connector 16 is coupled to the electrical conductor 14 at the terminal end 32 of the housing 12 and generally extends along the longitudinal axis 33. The connector 16 has a terminal surface 22 spaced from the housing 12. In one construction, the electrical conductor 14 is a USB printed circuit board (PCB), which is known in the art. The electrical conductor 14 may include an integral USB plug as the connector 16. However, any similar media having the necessary electrical componentry to enable illumination of a light emitter 18 can be used as the electrical conductor 14 (i.e., a small drop resister). Thus, in this configuration, as shown in FIG. 4, the electronic conductor assembly 70 is a mass storage device such as a flash drive having a USB plug as a connector 14. Alternatively, the electronic conductor assembly 10 or 80 may be a plug at one end of a USB cable as shown in FIGS. 1 and 5. The USB cable may include multiple connectors 14, such as a USB plug or any other type of plug or receptacle configuration required by different OEM requirements, on at least two terminal ends of the USB cable. Currently there are several USB connector configurations on the market, including, Standard A, Standard B, Mini-A, Mini-B, Micro-A and Micro-B. Thus, the USB cable may include on one end of the cable, a USB Standard A plug, while the other end of the cable may be a Micro-B, Mini-B, or Standard B plug. Although the other end of the cable may instead be a Micro-A plug or a Standard A plug, these configurations do not meet the USB standard.

For purposes of this disclosure, the light emitter 18 is a light emitting diode (LED) light bulb secured or bonded to the electrical conductor 14. While the light emitter 18 can be other types of lights known in the art, an LED light has been found to be satisfactory as LED lights do not generate a significant amount of heat and use less energy than other types of bulbs, such as incandescent and fluorescents. Further, although only one light emitter 18 is shown, it should be appreciated that more than one light emitter can be used. The bonding of the LED light to the electrical conductor 14 can be formed by a variety of conductive connecting materials known in the art, including but not limited to solder and adhesives.

The light guide 20 or 82 is positioned substantially within the housing to direct light from the light emitter 18 to exit the housing 12 from the terminal end 32. In one configuration, the light guide 20 includes a translucent housing. Acrylic plastic has been found to be satisfactory materials for the light guide 20 or 82. In another configuration, the light guide 82 is coupled to or is part of a housing of the light emitter 18.

As shown in FIGS. 2 and 4, the light guide 20 includes a substantially annular front surface 44 having an opening 46 for receiving the connector 16, a top wall 52 and bottom wall 54, and two sidewalls 56, 58. The front surface 44 of the light guide 20 substantially aligns with the terminal end 32 of the housing 12. In the assembled configuration, the front surface 44 of the light guide 20 abuts the circumference of the connector 16 to provide 360 degrees of illumination around the connector 16. The light guide 20, in certain configurations also includes an indicator 62 which extends through an opening 64 in the top portion 66 of the housing 12 such that a top portion 68 of the indicator 62 is exposed and substantially flush with the top portion 66 of the housing 12. The indicator 62 may further include an alignment tab 72 for engaging a rim 74 on the top portion 66 of the housing 12. The indicator 62 passes light when the light emitter 18 receives power (and generates light). Thus, illumination of the indictor 62 indicates the light emitter 18 is receiving power. In one configuration, the light guide 20 can include at least one reflector (not shown) for directing (reflecting) the light from the light emitter 18 to the front surface 44 of the light guide 20. Thus, the light is projected from the terminal end 32 of the housing 12 around the entire circumference of the connector 14 and in some embodiments, through an indicator 62, without also projecting through other portions of the housing 12. This provides, among other things, light sufficient for illuminating the connector 16 and a receiving area on a device, such as a USB receptacle of a device.

The light from the light emitter 18 may further be directed through both the light guide 20 and the connector 16 as shown in FIG. 4. Thus, light can be projected substantially along the longitudinal axis about the periphery of the connector, or within the periphery of the connector or both about and within the periphery of the connector.

That is, in a further construction, as shown in FIG. 5, the light from the light emitter 18 may instead be directed solely within a periphery of the connector 16 from the terminal end 32 of the electrical connector assembly 80 towards the terminal surface 22 of the connector 16 by light guide 82. While this construction can be used with any connector type, it has been found to be satisfactory for USB Standard A plug types.

The lighted electrical connector assembly 10, 50, 60, 70, 80 can be designed to be powered by a battery or the USB interface, that is, a USB connection between one of multitude electrical connector assemblies connected to a powered host device. In the battery powered configuration, such as that shown in FIG. 4, the electrical connector assembly 70 includes a rechargeable battery 84. The rechargeable battery 84 may be configured to be recharged with the USB interface. In this configuration, power is drawn from a host computer or device and stored in the battery 84. The battery 84 then provides power to the light emitter 18 when a switch button 86 is activated. In certain embodiments, the switch button 86 allows selective switching between various illumination modes such as increasing light levels of the light emitter. The electrical connector assembly 70 in this configuration may include a control circuit (not shown) to control the illumination mode of the light emitter when the switch button 86 is activated and a mode is selected.

The switch button 86 may be located in an opening 88 of the housing 12. That is, in one configuration, both the light guide 20 or 82 and the indicator 62 are illuminated when the switch button 86 is activated.

In another configuration, the indictor 62 is illuminated by the same LED as the light guide 20, indicating power is being received from a sole power source, either a battery 84 or USB. Alternatively the indicator 62 may be illuminated by a different LED and power source. In this configuration, one light emitter illuminates the light guide 20 that is powered by the rechargeable battery 84 to provide illumination for accurate placement of the connector 16 into the receptacle while a different light emitter (not shown) illuminates the indicator 62 indicating power is received from a USB power source when the connector 16 is successfully inserted into the receptacle 24.

While the invention has been described in connection with a particular embodiment, it is not intended to limit the scope of the invention to the particular form set forth, but on the contrary, it is intended to cover such alternatives, modifications, and equivalents as may be included within the spirit and scope of the invention as defined by the appended claims.

The invention claimed is:

1. An electrical connector assembly, comprising:

(a) an electrical conductor;

(b) a housing enclosing a portion of the conductor, the housing having a first outer surface, a second outer surface and a terminal end;

(c) a connector connected to the conductor and the housing, the connector having an exposed length extending along a longitudinal axis from the terminal end of the housing, the connector having a terminal surface spaced from the housing, the exposed length being intermediate the housing and the terminal surface;

(d) a light emitter within the housing;

(e) a light guide substantially within the housing to direct light from the light emitter to exit the housing from the terminal end to substantially illuminate the exposed length of the connector along the longitudinal axis; and (f) an indicator in the housing and exposed at the first outer surface, the indicator transmitting light from the light emitter to provide an orientation indication of the housing, wherein the light guide directs a first portion of the light to pass through the terminal end of the connector and a second portion of the light to pass through the indicator to indicate a power status, and wherein the connector has a USB configuration.

2. The electrical connector assembly of claim 1, wherein the electrical conductor supplies power to the light emitter.

3. The electrical connector assembly of claim 1, wherein the light emitter is an LED.

4. The electrical connector assembly of claim 1, further comprising a battery in the housing.

5. The electrical connector assembly of claim 1, wherein the terminal surface is transverse to the longitudinal axis.

6. The electrical connector assembly of claim 1, wherein the light guide is annular.

7. The electrical connector assembly of claim 1, wherein the electrical conductor includes a twisted pair of wires.

8. The electrical connector assembly of claim 1, further comprising a magnetic memory within the housing, and the electrical conductor is connected to the memory.

9. The electrical connector assembly of claim 1, wherein the housing is substantially opaque.

10. The electrical connector assembly of claim 1, wherein the indicator is adjacent the terminal end of the housing.

11. An electrical connector assembly, comprising:

(a) an electrical conductor;

(b) a housing enclosing a portion of the conductor, the portion having a terminal end;

(c) a connector connected to the conductor and the housing, the connector extending along a longitudinal axis from the terminal end of the housing, the connector having a terminal surface spaced from the housing, the terminal surface having a periphery;

(d) a light emitter within the housing; and (e) a light guide substantially within the housing to direct a portion of the light from the light emitter, wherein the light guide directs a first portion of the light to pass through the terminal surface of the connector and a second portion of the light to pass through an indicator to indicate a power status, and wherein the connector has a USB configuration.

12. The electrical connector assembly of claim 11, wherein the light guide directs a portion of the light to intersect a portion of the connector.

13. The electrical connector assembly of claim 11, wherein the electrical conductor includes a twisted pair of wires.

14. The electrical connector assembly of claim 11, further comprising a magnetic memory within the housing, and the electrical conductor is connected to the memory.

15. The electrical connector assembly of claim 11, wherein the housing is substantially opaque.

16. The electrical connector assembly of claim 11, wherein the housing includes a first outer surface and further comprising an indicator exposed to the first outer surface adjacent to the terminal surface, the indicator being illuminated and indicating an orientation of the housing.

* * * * *